US006635286B2

(12) United States Patent
Hei et al.

(10) Patent No.: US 6,635,286 B2
(45) Date of Patent: Oct. 21, 2003

(54) PEROXY ACID TREATMENT TO CONTROL PATHOGENIC ORGANISMS ON GROWING PLANTS

(75) Inventors: Robert D. P. Hei, Baldwin, WI (US); John Dennis Hilgren, Shoreview, MN (US); Joy Ann Salverda, Woodbury, MN (US); Brandon Leon Herdt, Hastings, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/896,807

(22) Filed: Jun. 29, 2001

(65) Prior Publication Data

US 2003/0026846 A1 Feb. 6, 2003

(51) Int. Cl.$^7$ ................................................ A01N 25/04
(52) U.S. Cl. .................... 424/616; 424/405; 424/406; 500/320; 514/557; 514/558; 514/559; 514/560
(58) Field of Search ................. 424/405, 406, 424/44, 616; 504/100, 101, 113, 114, 116, 125, 320; 514/557–560, 155, 578

(56) References Cited

U.S. PATENT DOCUMENTS

| 2,512,640 | A | 6/1950 | Greenspan et al. |
| 5,168,655 | A | 12/1992 | Davidson et al. |
| 5,200,189 | A | 4/1993 | Oakes et al. |
| 6,024,986 | A | 2/2000 | Hei |
| 6,165,483 | A | 12/2000 | Hei et al. |
| 6,238,685 | B1 | 5/2001 | Hei et al. |

FOREIGN PATENT DOCUMENTS

| DE | 3003875 | 8/1981 |
| DK | 9300538 | 11/1994 |
| EP | 0 242 990 | 10/1987 |
| EP | 0 361 955 | 4/1990 |
| GB | 2 187 958 | 3/1987 |
| GB | 2 257 630 | 7/1991 |
| JP | 7031210 | 2/1995 |
| JP | 7258005 | 10/1995 |
| WO | WO 94/06294 | 3/1994 |

Primary Examiner—Neil S. Levy
(74) Attorney, Agent, or Firm—Merchant & Gould P.C.

(57) ABSTRACT

A method of using peracid/acid compositions, where the mole ratio of acid to peracid is less than about 3:1, to treat field or greenhouse grown plant tissue, seeds, fruits, and growing media and containers is described. The peracid/acid system can lower the natural, plant pathogen and human pathogenic microbial load resulting in less waste to molding, spoilage, and destruction because of pathogenic poisons.

18 Claims, No Drawings

PEROXY ACID TREATMENT TO CONTROL PATHOGENIC ORGANISMS ON GROWING PLANTS

FIELD OF THE INVENTION

The invention relates to a process of using peracid compositions mixed with another short-chain fatty acid to treat field, hydroponic or greenhouse growing plant tissue, seeds, fruits, growing media, storage facilities and equipment, and containers. The peracid can lower the natural, plant pathogen and human pathogenic microbial load resulting in less waste to molding, spoilage, and destruction because of pathogenic poisons.

BACKGROUND OF THE INVENTION

In the production of fruits and vegetables, plants can be grown in the field, in greenhouses, and hydroponically. Each location has its own growing medium, environment and growing conditions. Agricultural personnel work to maximize production by maximizing growing conditions while minimizing attack on seeds, seedlings, plants and fruit by living pests. Such pests include insects, rodents, bacteria, fungi, etc.

Substantial attention has been given to antimicrobial compounds that attack bacteria and fungi on seeds, seedlings, growing plants and fruit in the production cycle on growing plants. The use of fungicides in agriculture is necessitated by the great losses caused by a wide variety of plant-pathogenic microorganisms. To be economic, the costs of controlling plant diseases by the application of bactericides and fungicides must be offset by potential gains of several fold. Large tonages of fungicides are required in the agriculture of apples, pears, bananas, cereals, cocoa, coffee, cotton, potatoes, tobacco, grapes, sprouts and other common fruits and vegetables including celery, leeks, onions, lettuce, spinach, brussel sprouts, potatoes, truffles, garlic, shallots, peppers, beans, tomatoes, almonds, pears, apples, peanuts and others. Fungicides are typically applied in water suspension with hydraulic sprayers or in the form of dust, granules or fumigants. Early fungicides included sulfur and polysulfides, heavy metals and others. Such harsh fungicides have been replaced by newer but still toxic materials such as quinones, organosulfur compounds, imidazolines and guanidines, trichloromethylthiocarboximides, chlorinated and nitrated benzenes, oxithines, benzimidazoles, pyrimidines, and others. These broad spectrum protectant materials effect enzyme and membrane systems of the target microorganism. Typically, the mode of action includes inhibition of fungal or bacterial energy production, interference with biosynthesis or disruption of cell membrane structure.

The above fungicides have had some success; however, they are viewed as toxic materials and a substantial quantity of plant produce is wasted due to their deleterious effect.

Further, human and plant pathogenic bacteria and fungi can be a contamination problem in growing plants. We have found coli form, salmonella, and other bacteria common in the agricultural and greenhouse environment can contaminate growing plants and pose a threat to human health in consumption of fresh vegetables, fruit and produce.

Peroxy acids are strong oxidizers and have the simple general structure given as formula (1), where R can be essentially any hydrocarbon group:

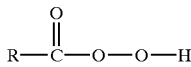

(1)

Peroxy-containing compositions have been described for use in the production of microbicidal agents. However, very few peroxy systems have addressed protection of growing plants from bacterial contamination. Accordingly, a substantial need exists to develop antimicrobial materials that can be used directly to protect growing plants including seeds, cuttings, seedlings, plant parts, fruit, and other agricultural produce.

SUMMARY OF THE INVENTION

We have found that a mixed peracid/acid treatment composition can be used to protect growing plant tissue from the undesirable effects of microbial attack. The peracid/acid composition used in this invention can be applied to growing plant tissues and can provide residual antimicrobial effects after the plant has completed its growth cycle, fruit or vegetable material have been harvested and sent to market. The composition of the invention has been found to have excellent antimicrobial effects but poses little toxic effects to agricultural workers or the ultimate consumer.

We have found that peroxy acid/acid compositions can be an effective treatment of living or growing plant tissues including seeds, roots, tubers, seedlings, cuttings, rooting stock, growing plants, produce, fruits and vegetables, etc. Under certain circumstances, a single peroxyacid/acid composition can be effective; however, in other circumstances, a mixed peroxy acid/acid composition has substantially improved and surprising properties.

The invention involves a peroxyacid antimicrobial concentrate and diluted end use composition including an effective microbicidal amount of one or more aliphatic $C_2$–$C_{12}$ peroxycarboxylic acids and an aliphatic $C_3$–$C_{12}$ carboxylic acid wherein the mole ratio of aliphatic carboxylic acid to peroxycarboxylic acid is less than about 3:1. The concentrate composition can be diluted with a major proportion of water to form an antimicrobial sanitizing use solution having a pH in the range of about 2 to 8, with a peroxycarboxylic acid concentration of at least about 5 ppm, preferably about 30 to 5000 ppm, and most preferably about 200 to 1000 ppm. Other components may be added such as a hydrotrope coupling agent for solubilizing the peroxyfatty acid in the concentrate form and when the concentrate composition is diluted with water.

The invention involves a method of controlling microbial pathogens on living plant tissue by treating said plant tissue with a dilute aqueous solution containing an effective amount of one or more aliphatic $C_2$–$C_{12}$ peroxycarboxylic acids and an aliphatic $C_3$–$C_{12}$ carboxylic acid, wherein the mole ratio of aliphatic carboxylic acid to percarboxylic acid is less than about 3:1.

The invention further involves a method for controlling microbial pathogens on living plant tissue by diluting in an aqueous liquid a concentrate containing: about 0.1 to 25 wt-% of one or more aliphatic $C_2$–$C_{12}$ peroxycarboxylic acids and about 0.01 to 30 wt-% of an aliphatic $C_3$–$C_{12}$ carboxylic acid, wherein the mole ratio of aliphatic carboxylic acid to percarboxylic acid is less than about 3:1, to form a solution; and contacting said plant tissue with said solution.

The invention further involves a method for controlling microbial pathogens on living plant tissue by diluting in an aqueous liquid a concentrate containing: about 0.1 to 25 wt-% of one or more $C_1$–$C_7$ aliphatic peroxycarboxylic acids; about 0.01 to 20 wt-% of one or more $C_8$–$C_{12}$ aliphatic peroxycarboxylic acids; about 0.01 to 30 wt-% of one or more $C_3$–$C_{12}$ aliphatic carboxylic acid; and about 1 to 30 wt-% of hydrogen peroxide to form a solution, wherein the mole ratio of aliphatic carboxylic acid to percarboxylic acid is less than about 3:1; and contacting said growing plants with said solution.

As the term is used herein, a $C_2$–$C_{12}$ peroxyacid may be interchangeably used with a $C_2$–$C_{12}$ aliphatic peroxycarboxylic acid or $C_2$–$C_{12}$ peracid. These terms are intended to mean the product of the oxidation of a $C_2$–$C_{12}$ acid such as: a fatty acid, a dicarboxylic acid, a mono- or di-ester dicarboxylic acid, a hydroxy acid, a lactone, a tricarboxylic acid, or a mixture of these acids, to form a peroxyacid or mixture of peroxyacids having from about 2 to 12 carbon atoms per molecule. The $C_2$–$C_{12}$ peroxyacids are straight or branched aliphatic. The $C_2$–$C_{12}$ peroxyacids can be equilibrium derived, i.e. from a mixture of peracid, its corresponding carboxylic acid and hydrogen peroxide, such as is common for peracetic acid, perglycolic acid, permalonic acid, perlactic acid, peroctanoic acid, perhydroxycaproic acid, perhydroxycaprylic acid, mono-methyl peradipate, mono-methyl persuccinate, mono-methyl perglutarate, mono-ethyl peradipate, mono-ethyl persuccinate, mono-ethyl perglutarate, mono-isobutyl peradipate, mono-isobutyl persuccinate, mono-isobutyl perglutarate, and the like. The $C_2$–$C_{12}$ peroxyacids can also be isolated peracids such as perheptanoic acid, peroctanoic acid, and perdecanoic acid.

In a preferred embodiment, the claimed invention includes a method of controlling microbial pathogens on living plant tissue. This treatment utilizes a combination of two different peroxy acids and another carboxylic acid. This mixture comprises at least 4 parts per million (ppm) of a smaller $C_2$–$C_7$ peroxy carboxylic acid, at least 1 ppm of a larger $C_8$–$C_{12}$ peroxy carboxylic acid, and at least 0.1 ppm of a $C_3$–$C_{12}$ aliphatic carboxylic acid. The more preferred mixture comprises at least 20 ppm of a smaller $C_2$–$C_7$ peroxy acid and at least 2 ppm of an aliphatic $C_8$–$C_{12}$ peroxy acid, and at least 5 ppm of an aliphatic $C_3$–$C_{12}$ carboxylic acid.

An especially preferred embodiment of the composition includes a mixture of peroxyacetic acid, formula (2), and peroctanoic acid, formula (3), with a $C_3$–$C_{12}$ aliphatic carboxylic acid, such as propionic, hexanoic, heptanoic, octanoic, nonanoic, decanoic or a mixture thereof.

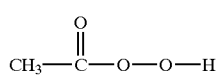
(2)

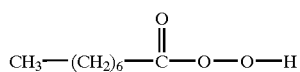
(3)

Another especially preferred embodiment of the composition includes individual component, or mixtures, of the mono-methyl esters of peroxyadipic acid, peroxysuccinic acid, and peroxyglutaric acid, formula (4), and generically described as monoester peracids derived from diacids or diesters, e.g., such as adipic, succinic, glutaric, or malonic acid and mixtures thereof.

(4)

where R and R' are linear or branched aliphatic $C_1$–$C_6$ hydrocarbons.

The composition also may contain a hydrotrope or surfactant for the purpose of increasing the aqueous solubility of various slightly soluble organic compounds. The preferred embodiment of the invention utilizes a hydrotrope chosen from the group of n-octanesulfonate, dodecylbenzene sulfonate, a xylene sulfonate, cumene sulfonate, an alkyl naphthalene sulfonate, 2-ethylhexyl sulfate, lauryl sulfate, lauryl ether sulfate, an amine oxide, a nonionic surfactant, or a mixture thereof.

The composition may also contain a chelating agent for the purpose of removing ions from solution. The preferred embodiment of the invention uses 1-hydroxyethylidene-1,1-diphosphonic acid.

Further, the invention also provides a method of growing at least one plant on a hydroponic substrate in a hydroponic liquid supply medium to produce usable fruit or vegetable products with reduced microbial contamination, the method including the steps of: (a) establishing growing and living plant tissue in the hydroponic substrate; (b) contacting the living plant tissue, the hydroponic substrate and the hydroponic liquid with a dilute aqueous solution containing an effective amount of one or more $C_2$–$C_{12}$ percarboxylic acids and an aliphatic $C_3$–$C_{12}$ carboxylic acid, wherein the mole ratio of aliphatic carboxylic acid to peroxycarboxylic acid is less than about 3:1; and (c) harvesting an improved product.

DETAILED DESCRIPTION OF THE INVENTION

Peracids

We have found surprisingly that peroxy acid compounds mixed with another $C_3$–$C_{12}$ fatty acid can be contacted directly with living plant tissue in the form of a seed, a cutting, a root stock, graft, tuber juvenile or adult plant and reduce microbial populations without substantially affecting the health of the living tissue.

Moreover we have found that when a $C_8$–$C_{12}$ peroxyacid is combined with a $C_2$–$C_7$ peroxycarboxylic acid and another aliphatic $C_3$–$C_{12}$ carboxylic acid, a synergistic effect is produced and greatly enhanced antimicrobial activity is exhibited when compared to the $C_8$–$C_{12}$ peroxyacid or the $C_2$–$C_7$ peroxycarboxylic acid alone. For example, a blend of a $C_8$–$C_{12}$ peroxyacid, a $C_2$–$C_7$ peroxycarboxylic acid and a $C_3$–$C_{12}$ aliphatic carboxylic acid can effectively kill microorganisms (e.g., a 5 log10 reduction in 30 seconds) from a concentration level below 100 ppm and as low as 20 ppm of the peracid blend.

A variety of $C_2$–$C_{12}$ aliphatic peroxyacids may be employed in the composition of the invention such as peroxyfatty acids and monoester-monoperoxydicarboxylates and monoperoxy- or diperoxy-dicarboxylic acids. The $C_2$–$C_{12}$ peroxyacids employed in the present invention may be structurally represented as: $R_1$—$CO_3H$, wherein $R_1$ is a hydrocarbon moiety having from about 1 to 11 carbon atoms. $R_1$ may have substituents in or at the end of the chain, e.g., —OH, —$CO_2R_1$ (e.g., as in monoester dicarboxylates), or heteroatoms (e.g.,-0-as in alkylether carboxylic acids), as long as the antimicrobial properties of the overall composition are not significantly affected. It should be recognized that "$R_1$" substituents or heteroatoms may change the overall acidity (i.e., pKa) of the carboxylic acids herein described. Such modification is within the contemplation of the present invention provided the advantageous antimicrobial performance is maintained. Furthermore, $R_1$ may be linear or branched. Preferred hydrocarbon moieties (i.e. preferred $R_1$'s) include linear, saturated, hydrocarbon aliphatic moieties having from 1 to 3 and 7 to 11 carbon atoms (or 2 to 4 and 8 to 12 carbon atoms per molecule), and hydrocarbon aliphatic carboxylic ester moieties having 1 to 4 carbon atoms in the hydrocarbon ester function (e.g., methyl propionate or methyl ethanoate or methyl butanoate substituents).

The $C_2$–$C_7$ peroxycarboxylic acids can be derived from a $C_2$–$C_7$ carboxylic acid or dicarboxylic acid by reacting the acid, or the corresponding anhydride or acid chloride, or $C_1$–$C_6$ ester, or lactone with hydrogen peroxide. Examples of suitable $C_2$–$C_7$ carboxylic acids include acetic acid, propionic acid, glycolic acid, and alpha-hydroxyheptanoic acid, or their corresponding anhydrides or acid chlorides or $C_1$–$C_6$ esters or lactones. Preferable $C_2$–$C_7$ peroxycarboxylic acids for use in the composition of the invention include peroxyacetic acid, peroxypropionic acid, peroxyglycolic acid, or mixtures thereof.

Specific examples of suitable $C_8$–$C_{12}$ carboxylic fatty acids which can be reacted with hydrogen peroxide to form peroxyfatty acids include such saturated fatty acids as caprylic (octanoic) ($C_8$), pelargonic (nonanoic) ($C_9$), capric (decanoic) ($C_{10}$), undecyclic (undecanoic) ($C_{11}$), lauric (dodecanoic) ($C_{12}$), or alpha-hydroxyoctanoic ($C_8$). These acids can be derived from both natural and synthetic sources. Natural sources include animal and vegetable fats or oils which should be fully hydrogenated. Synthetic acids can be produced by the oxidation of petroleum wax. Particularly preferred peroxyfatty acids for use in the composition of the invention are linear monoperoxy aliphatic fatty acids such as peroxyoctanoic acid, peroxydecanoic acid, or mixtures thereof.

Other suitable peroxyacids are derived from the oxidation of dicarboxylic acids, $C_1$–$C_6$ esters, and anhydrides. Suitable dicarboxylic acids, $C_1$–$C_6$ esters, and anhydrides include those of malonic, adipic, glutaric, succinic, sebacic acid ($C_{10}$). These acids, $C_1$–$C_6$ esters, and anhydrides can be reacted with hydrogen peroxide to form the peracid form suitable for use in the composition of the invention. Preferred peracids in this group include monoester-monoperoxy- or monocarboxylate-monoperoxy- or diperoxyadipic acid, monoester-monoperoxy- or monocarboxylate-monoperoxy- or diperoxysuccinic acid, monoester-monoperoxy- or monocarboxylate-monoperoxy- or diperoxyglutaric acid, and monocarboxylate-monoperoxy- or monoester-monoperoxy- or diperoxysebacic acid, or mixtures thereof.

The above peroxyacids provide antibacterial activity against a wide variety of microorganisms, such as gram positive (e.g., *Staphylococcus aureus*) and gram negative (e.g., *Escherichia coli, salmonella*, etc.) microorganisms, yeast, molds, bacterial spores, etc. When the above $C_8$–$C_{12}$ peroxyacids are combined with a $C_2$–$C_7$ peroxycarboxylic acid, greatly enhanced activity is shown compared to the $C_2$–$C_7$ peroxycarboxylic acid alone or the $C_8$–$C_{12}$ peroxycarboxylic acid alone.

The antimicrobial concentrate of the present invention can contain about 0.1 to 25 wt. %, preferably about 0.5 to 20 wt. %, and most preferably about 0.4 to 15 wt. % of a $C_2$–$C_{12}$ peroxyacid, and about 0.01 to 30 wt. %, preferably about 0.1 to 10 wt. % and most preferably 0.4–5 wt. % of an aliphatic $C_3$–$C_{12}$ carboxylic acid. The concentrate composition preferably has a molar ratio of $C_3$–$C_{12}$ carboxylic acid to $C_2$–$C_{12}$ peroxycarboxylic acid of about 0.01:1 to 3:1. The concentrate contains sufficient acid so that the end use solution has a pH of about 2 to 8, preferably about 3 to 7. Some acidity may come from an inert acidulant which may be optionally added (e.g., sulfuric or phosphoric acid).

In another embodiment of the present invention, the antimicrobial concentrate can contain about 0.1 to 20 wt. %, preferably about 0.1 to 5 wt. %, and most preferably about 0.5 to 2 wt. % of a $C_8$–$C_{12}$ peroxyacid, and about 0.1 to 25 wt. %, preferably about 1 to 20 wt. %, and most preferably 4–15 wt. % of a $C_2$–$C_7$ peroxycarboxylic acid, and about 0.01 to 30 wt. %, preferably about 0.1–10 wt. %, and most preferably 0.5–5 wt. % of an aliphatic $C_3$–$C_{12}$ carboxylic acid. The concentrate composition preferably has a molar ratio of $C_3$–$C_{12}$ carboxylic acid to $C_2$–$C_{12}$ peroxycarboxylic acid of about 0.01:1 to 3:1. The concentrate composition preferably has a weight ratio of $C_2$–$C_4$ peroxycarboxylic acid to $C_8$–$C_{12}$ peroxylic acid of about 15:1 to 1:1. The concentrate contains sufficient acid so that the end use solution has a pH of about 1 to 8, preferably about 1 to 5. Some acidity may come from an inert acidulant which may be optionally added (e.g., sulfuric or phosphoric acid).

The peracid components used in the composition of the invention can be produced in a simple manner by mixing a hydrogen peroxide ($H_2O_2$) solution, or by utilizing powdered peroxide generators such as percarbonates, persulfates, magnesium peroxide, calcium peroxide, or perborates, with the desired amount of acid. With the higher molecular weight fatty acids, a hydrotrope coupler may be required to help solubilize the fatty acid. The $H_2O_2$ solution also can be added to previously made peracids such as peracetic acid or various perfatty acids to produce the peracid composition of the invention. The concentrate can contain about 1 to 40 wt. %, preferably about 5 to 25 wt. % of hydrogen peroxide.

The concentrate composition can further include a $C_3$–$C_{12}$ aliphatic carboxylic acid, a free $C_8$–$C_{12}$ carboxylic acid, a free $C_2$–$C_7$ carboxylic acid, or mixtures thereof. The free acids will correspond to the starting materials used in the preparation of the peroxyacid components and can be present as a result of an equilibrium reaction with the hydrogen peroxide to form the peroxyacids. The composition of the present invention includes, however, at least one other $C_3$–$C_{12}$ aliphatic carboxylic acid. Preferred $C_3$–$C_{12}$ aliphatic carboxylic acids include propionic, hexanoic, heptanoic, octanoic, nonanoic, decanoic, or mixtures thereof in amounts defined above.

Other Components

Various optional materials may be added to the composition of the invention to help solubilize the fatty acids, restrict or enhance the formation of foam, to control hard water, to stabilize the composition, or to further enhance the antimicrobial activity of the composition.

The composition of the invention can contain a surfactant hydrotrope coupling agent or solubilizer that permits blending short chain perfatty acids in aqueous liquids. Functionally speaking, the suitable couplers which can be employed are non-toxic and retain the fatty acid and the perfatty acid in aqueous solution throughout the temperature range and concentration to which a concentrate or any use solution is exposed.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and $C_8$–$C_{10}$ alkyl glucosides. Preferred coupling agents for use in the present invention include n-octanesulfonate, available as NAS 8D from Ecolab, n-octyl dimethylamine oxide, and the commonly available aromatic sulfonates such as the alkyl benzene sulfonates (e.g. xylene sulfonates) or naphthalene sulfonates. Preferred anionic surfactants include $C_6$–$C_{24}$ alkylbenzene sulfonates; $C_6$–$C_{24}$ olefin sulfonates; $C_6$–$C_{24}$ paraffin sulfonates; cumene sulfonate; xylene sulfonate; $C_6$–$C_{24}$ alkyl naphthalene sulfonates; $C_6$–$C_{24}$ alkyl or dialkyl diphenyl ether sulfonates or disulfonates, $C_4$–$C_{24}$ mono or dialkyl sulfosuccinates; sulfonated or sulfated fatty acids; $C_6$–$C_{24}$ alcohol sulfates (preferably $C_6$–$C_{12}$ alcohol sulfates); $C_6$–$C_{24}$ alcohol ether sulfates having 1 to about 20 ethylene oxide groups; and $C_4$–$C_{24}$ alkyl, aryl or alkaryl phosphate esters or their alkoxylated analogues having 1 to about 40 ethylene, propylene or butylene oxide units or mixtures thereof.

Other preferred hydrotropes include nonionic surfactants of $C_6$–$C_{24}$ alcohol ethoxylates (preferably $C_6$–$C_{14}$ alcohol ethoxylates) having 1 to about 20 ethylene oxide groups (preferably about 9 to about 20 ethylene oxide groups); $C_6$–$C_{24}$ alkylphenol ethoxylates (preferably $C_8$–$C_{10}$ alkylphenol ethoxylates) having 1 to about 100 ethylene oxide groups (preferably about 12 to about 20 ethylene oxide groups); $C_6$–$C_{24}$ alkylpolyglycosides (preferably $C_6$–$C_{20}$ alkylpolyglycosides) having 1 to about 20 glycoside groups (preferably about 9 to about 20 glycoside groups); $C_6$–$C_{24}$ fatty acid ester ethoxylates, propoxylates or glycerides; and $C_4$–$C_{24}$ mono or dialkanolamides. A particularly useful nonionic surfactant for use as a defoamer is nonylphenol having an average of 12 moles of ethylene oxide condensed thereon, it being encapped with a hydrophobic portion comprising an average of 30 moles of propylene oxide.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present compositions control.

The hydrotrope coupling agent can comprise about 0 to 30 wt. %, preferably about 1 to 15 wt. %, and most preferably about 2 to 15 wt. % of the concentrate composition.

Compounds such as mono, di and trialkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation herein. Such materials tend to enhance performance of the other components of the composition. Chelating agents can be added to the composition of the invention to enhance biological activity, cleaning performance and stability of the peroxyacids. For example, 1-hydroxyethylidene-1,1-diphosphonic acid commercially available from the Monsanto Company under the designation "DEQUEST" has been found to be effective. Chelating agents can be added to the present composition to control or sequester hardness ions such as calcium and magnesium. In this manner both detergency and sanitization capability can be enhanced. These stabilizers and chelating agents can desirably be employed to improve the storage stability of solutions according to the invention and are especially desirable where the proposed application involves the likely chance that the peracid will be contacted with compounds known to cause decomposition, for example transition metal ions. Preferred chelating agents are often aminopolycarboxylic acids or salts thereof such as EDTA, HEDTA, or DTPA, and/or carboxylic acid substituted N-containing heterocyclics, such as picolinic or dipicolinic acid, 8-hydroxyquinoline, and organopolyphosphonates, including 1-hydroxyethylidene-1,1-diphosphonic acid (HEDP), and alkyleneaminomethylene phosphonic acids such as ethylene diamino tetra-methylene phosphonic acid, cyclohexane-1,2-diaminotetramethylene phosphonic acid and diethylenetriaminepenta methylene phosphonic acid. A combination of an organophosphonate and EDTA is particularly suitable. The amount of chelant in the solution is at the discretion of the formulator, but is preferably greater than 0.05% and often not greater than about 5.5%, calculated as active material therein.

Other materials which are sufficiently stable at the low pH contemplated by the present composition may be added to the composition to impart desirable qualities depending upon the intended ultimate use. For example, phosphoric acid ($H_3PO_4$), or sulfuric acid ($H_2SO_4$), can be added to the composition of the invention. Additional compounds can be added to the concentrate (and thus ultimately to the use solution) to change its color or odor, to adjust its viscosity, to enhance its thermal (i.e., freeze-thaw) stability or to provide other qualities which tend to make it more marketable.

The composition of the invention can be made, for example, by simply mixing an effective amount of a $C_8$–$C_{12}$ peroxyacid such as a peroxyfatty acid, e.g. peroxyoctanoic acid, with some source of a $C_2$–$C_7$ peroxycarboxylic acid, such as peroxyacetic acid, and an aliphatic $C_3$–$C_{12}$ carboxylic acid. This composition would be formulated with preformed peroxyoctanoic acid and preformed peroxyacetic acid. A preferred composition of the invention can be made by mixing a $C_2$–$C_7$ carboxylic acid, a $C_8$–$C_{12}$ carboxylic acid, a coupler and a stabilizer and reacting this mixture with hydrogen peroxide. A stable equilibrium mixture is produced containing a $C_2$–$C_7$ peroxycarboxylic acid and a $C_8$–$C_{12}$ peroxyacid by allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, a $C_2$–$C_7$ carboxylic acid, a $C_8$–$C_{12}$ carboxylic acid, a $C_2$–$C_7$ peroxycarboxylic acid, a $C_8$–$C_{12}$ peroxycarboxylic acid, water, and various couplers and stabilizers. Once equilibrium is reached, another carboxylic acid is added to the mixture. This is an aliphatic $C_3$–$C_{12}$ carboxylic acid.

Method of Treatment

The present invention contemplates a concentrate composition which is diluted to a use solution prior to its utilization as a microbicide. Primarily for reasons of economics, the concentrate would normally be marketed and the end user would dilute the concentrate with water to a use solution. A preferred antimicrobial concentrate composition comprises about 0.1 to 5 wt. % of a $C_8$–$C_{12}$ peroxyfatty acid, about 1 to 20 wt. % of a $C_2$–$C_7$ peroxycarboxylic acid, about 0.4 to 5 wt-% of a $C_3$–$C_{12}$ aliphatic carboxylic acid, about 0 to 15 wt. % of a hydrotrope coupling agent, and about 1 to 30 wt. % of hydrogen peroxide. Other acidulants may optionally be employed in the composition such as phosphoric acid or sulfuric acid.

The level of active components in the concentrate composition is dependent upon the intended dilution factor and desired acidity in the use solution. The $C_8$–$C_{12}$ peroxyacid component is generally obtained by reacting a $C_8$–$C_{12}$ carboxylic acid with hydrogen peroxide in the presence of a $C_2$–$C_7$ carboxylic acid. Another $C_3$–$C_{12}$ aliphatic carboxylic acid is then added to the mixture. The resulting concentrate is diluted with water to provide the use solution. Generally, a dilution of 1 fluid oz. to 1–16 gallons (i.e. dilution of ~1 to ~2,000 by volume) of water can be obtained with 2% to 20% total peracids in the concentrate.

The compositions of the invention can be applied to growing plant tissue in a variety of techniques. The aqueous solution can be sprayed, painted, daubed, fogged, flooded onto or into the plant, the plant hydroponic substrate, the agricultural earth. The material can be reapplied periodically as needed.

EXAMPLES

Example 1

A rice-related mold, *Chaetomium funicola* (*C. funicola*), was treated using the following solutions. The compositions and controls were evaluated for antimicrobial activity using the procedure set out in *Germicidal and Detergent Sanitizing Action of Disinfectants,* Official Methods of Analysis of the Association of Official Analytical Chemists, paragraph 960.09 and applicable sections, 15th Edition, 1990 (EPA Guideline 91–2), using a 10 second contact time at 60° C.

The data shows that the limited effectiveness of individual antimicrobial materials such as solvents (Run #'s 1–2), carboxylic acids (Run #'s 3–4), peroxycarboxylic acids (Run #5), or binary mixtures without added carboxylic acids (Run #'s 6–8) yield substantially less microbial reduction of the mold than the C3–C12 carboxylic acid enhanced formulas (Run #'s 9–10).

TABLE 1

Peracid Improvements Using Fatty Acids

| Run # | 1 Peroxy Acid (ppm) | 2 Carboxylic Acid (ppm) | | 3 Solvent (%) | 4 Microbial Reduction (*C. funicola*) |
|---|---|---|---|---|---|
| 1 | 0 ppm | none | 0 ppm | benzyl alcohol (2.0%) | 0.1 |
| 2 | 0 ppm | none | 0 ppm | DBE-3 (2.0%) | 0.2 |
| 3 | 0 ppm | glycolic | 100,000 ppm | none (0.0%) | 0.2 |
| 4 | 0 ppm | octanoic | 800 ppm | none (0.0%) | 0.2 |
| 5 | 3000 ppm[1] | none | 0 ppm | none (0.0%) | 0.2 |
| 6 | 1500 ppm[2] | none | 0 ppm | benzyl alcohol (2.0%) | 1.4 |
| 7 | 1000 ppm[2] | none | 0 ppm | DBE-3 (1.5%) | 0.3 |
| 8 | 1500 ppm[2] | none | 0 ppm | DBE-3 (2.0%) | 4.8 |
| 9 | 1500 ppm[2] | octanoic | 800 ppm | DBE-3 (1.5%) | >6.5 |
| 10 | 1500 ppm[2] | octanoic | 800 ppm | benzyl alcohol (2.0%) | >5.0 |

[1]The active peracetic level from Oxonia Active; a commercial product from Ecolab Inc., St. Paul, MN
[2]Active peracetic acid concentration.

Example 2

Various screening organisms were treated using the following solutions. The compositions and controls were evaluated for antimicrobial activity using a 10 minute contact time at 25° C. The data shows the benefit of adding a $C_3$–$C_{12}$ carboxylic acid (octanoic acid) (Run #'s 6–8, 11–12) to a monoester-monoperoxy-dicarboxylate peracid blend, versus formulas without; especially with consideration to lowering the amount of active peroxycarboxylic acid required to achieve a passing result.

TABLE 2

Peracid Improvements Using Fatty Acids

| Run # | 1 Monoester Peroxy Acid[1] (ppm) | 2 Octanoic Acid (ppm) | 2 LAS (ppm) | 3 Screening Microbial | 4 Microbial Result |
|---|---|---|---|---|---|
| 1 | 180 ppm | 0 ppm | 0 ppm | *S. aureus* | passed |
| 2 | 180 ppm | 0 ppm | 60 ppm | *S. aureus* | passed |
| 3 | 120 ppm | 0 ppm | 0 ppm | *S. aureus* | passed |
| 4 | 120 ppm | 0 ppm | 70 ppm | *S. aureus* | passed |
| 5 | 90 ppm | 0 ppm | 0 ppm | *S. aureus* | failed |
| 6 | 90 ppm | 0 ppm | 40 ppm | *S. aureus* | failed |
| 6 | 63 ppm[2] | 40 ppm | 0 ppm | *S. aureus* | passed |
| 7 | 42 ppm[2] | 40 ppm | 80 ppm | *S. aureus* | passed |
| 8 | 42 ppm[2] | 40 ppm | 40 ppm | *S. aureus* | passed |
| 9 | 6636 ppm | 0 ppm | 0 ppm | *M. bovis* | failed |
| 10 | 531 ppm | 0 ppm | 500 ppm | *M. bovis* | failed |
| 11 | 531 ppm | 500 ppm | 0 ppm | *M. bovis* | passed |
| 12 | 531 ppm | 500 ppm | 500 ppm | *M. bovis* | passed |

[1]The active peracetic level from Perestane; SOLVAY S.A., 33 rue du Prince Albert, B-1050 Brussels, Belgium
[2]Buffered with 200 ppm citric acid

We claim:

1. A method for controlling microbial pathogens on living plant tissue comprising:

(a) diluting in an aqueous liquid a concentrate comprising:

(i) about 1 to 20 wt-% of an aliphatic $C_2$–$C_7$ peroxycarboxylic acid; and (ii) about 0.1 to 20 wt-% of an aliphatic $C_8$–$C_{12}$ peroxycarboxylic acid;

(iii) about 5 to 40 wt-% of an aliphatic $C_2$–$C_7$ carboxylic acid;

(iv) about 1 to 20 wt-% of an aliphatic $C_8$–$C_{12}$ carboxylic acid;
(v) about 1 to 30 wt-% of hydrogen peroxide; and
(vi) about 0.01 to 30 wt-% of another $C_3$–$C_{12}$ aliphatic carboxylic acid to form a solution, wherein the mole ratio of aliphatic carboxylic acid (vi) to peroxycarboxylic acid is less than about 3:1; and (b) contacting said plant tissue with said solution.

2. The process of claim 1, wherein the $C_2$–$C_7$ peroxycarboxylic acid is peroxyacetic acid, mono-methyl persuccinate, mono-methyl perglutarate, mono-methyl peradipate, mono-ethyl persuccinate, mono-ethyl perglutarate, or a mixture thereof.

3. The process of claim 1, wherein the $C_8$–$C_{12}$ aliphatic peroxycarboxylic acid is peroxyoctanoic acid, mono-ethyl peradipate, mono-isobutyl peradipate, mono-isobutyl persuccinate, mono-isobutyl perglutarate, or a mixture thereof.

4. The process of claim 1, wherein the $C_3$–$C_{12}$ aliphatic carboxylic acid (vi) is propionic acid, hexanoic acid, heptanoic acid, octanoic acid, decanoic acid, dodecanoic acid or a mixture thereof.

5. The process of claim 1, wherein the concentrate further comprises about 1 to 15 wt-% of a hydrotrope.

6. The process of claim 5, wherein the hydrotrope is n-octanesulfonate, a xylene sulfonate, an alkyl benzene sulfonate, an alkyl naphthalene sulfonate, an amine oxide, an alcohol ethoxylate, or a mixture thereof.

7. The process of claim 1, wherein the concentrate further comprises a chelating agent.

8. The process of claim 7, wherein the chelating agent is 1-hydroxyethylidene-1,1-diphosphonic acid.

9. A method of controlling microbial pathogens on living plant tissue comprising treating said plant tissue with diluted aqueous solution consisting essentially of:

(a) at least about 5 parts per million (ppm) of one or more aliphatic $C_2$–$C_7$ peroxycarboxylic acids; and
(b) at least about 0.1 part per million (ppm) of an aliphatic $C_8$–$C_{12}$ carboxylic acid, wherein the mole ratio of aliphatic carboxylic acid to peroxycarboxylic acid is less than about 3:1.

10. The method of claim 9, wherein the peroxycarboxylic acid is peroxyacetic acid, mono-methyl persuccinate, mono-methyl perglutarate, mono-methyl peradipate, mono-ethyl persuccinate, mono-ethyl perglutarate, or a mixture thereof.

11. The method of claim 9, wherein the aliphatic carboxylic acid is octanoic acid, decanoic acid, dodecanoic acid or a mixture thereof.

12. A method for controlling microbial pathogens on living plant tissue consisting essentially of:

(a) diluting in an aqueous liquid a concentrate comprising:
(i) about 0.1 to 25 wt-% of one or more aliphatic $C_2$–$C_7$ peroxycarboxylic acids; and
(ii) about 0.01 to 30 wt-% of an aliphatic $C_8$–$C_{12}$ carboxylic acid to form a solution; and (b) contacting said plant tissue with said solution, wherein the mole ratio of aliphatic carboxylic acid to peroxycarboxylic acid is less than about 3:1.

13. The process of claim 12, wherein the $C_2$–$C_7$ peroxycarboxylic acid is peroxyacetic acid, mono-methyl persuccinate, mono-methyl perglutarate, mono-methyl peradipate, mono-ethyl persuccinate, mono-ethyl perglutarate, or a mixture thereof.

14. The process of claim 12, wherein the aliphatic carboxylic acid is octanoic acid, decanoic acid, dodecanoic acid, or a mixture thereof.

15. The process of claim 12, wherein the concentrate further comprises about 1 to 15 wt-% of a hydrotrope.

16. The process of claim 15, wherein the hydrotrope is n-octanesulfonate, a xylene sulfonate, an alkylbenzene sulfonate, an alkyl naphthalene sulfonate, an amine oxide, an alcohol ethoxylate, or a mixture thereof.

17. The process of claim 12, wherein the concentrate further comprises a chelating agent.

18. The process of claim 17, wherein the chelating agent is 1-hydroxyethylidene-1,1-diphosphonic acid.

* * * * *